(12) United States Patent
Wu (10) Patent No.: US 9,248,305 B2
(45) Date of Patent: Feb. 2, 2016

(54) BUTTSTOCK

(71) Applicant: Chun-Hung Wu, New Taipei (TW)

(72) Inventor: Chun-Hung Wu, New Taipei (TW)

( * ) Notice: Subject to any disclaimer, the term of this patent is extended or adjusted under 35 U.S.C. 154(b) by 0 days.

(21) Appl. No.: 14/230,646

(22) Filed: Mar. 31, 2014

(65) Prior Publication Data

US 2014/0214106 A1    Jul. 31, 2014

(30) Foreign Application Priority Data

Dec. 31, 2013  (TW) .............................. 102224990 U (51) Int. Cl.
*A61N 1/39* (2006.01)
*F41C 23/22* (2006.01)

(52) U.S. Cl.
CPC .............. *A61N 1/3968* (2013.01); *F41C 23/22* (2013.01)

(58) Field of Classification Search
CPC ..... A61N 1/3925; A61N 1/3993; A61N 1/39; A61N 1/3968
See application file for complete search history.

(56) References Cited

U.S. PATENT DOCUMENTS

| | | | |
|---|---|---|---|
| 6,449,892 B1* | 9/2002 | Jenkins | 42/1.01 |
| 2003/0208237 A1* | 11/2003 | Locke et al. | 607/5 |
| 2004/0143297 A1* | 7/2004 | Ramsey, III | 607/5 |
| 2005/0115385 A1* | 6/2005 | Rodriguez et al. | 89/1.11 |

\* cited by examiner

*Primary Examiner* — Amanda Patton
*Assistant Examiner* — Philip Edwards
(74) *Attorney, Agent, or Firm* — Muncy, Geissler, Olds & Lowe, P.C.

(57) ABSTRACT

A buttstock includes a main body and a protecting member. The main body includes a shell member and an automated external defibrillator disposed in the shell member. The protecting member is movably connecting with the shell member of the main body so as to move relative to the shell member between a first position and a second position, wherein the protecting member shields the automated external defibrillator at the first position and exposes the automated external defibrillator at the second position respectively.

6 Claims, 11 Drawing Sheets

BUTTSTOCK

CROSS-REFERENCES TO RELATED APPLICATIONS

This non-provisional application claims priority under 35 U.S.C. §119(a) on Patent Application No. 102224990 filed in Taiwan, R.O.C. on 2013 Dec. 31, the entire contents of which are hereby incorporated by reference.

BACKGROUND

1. Technical Field

The disclosure relates to a buttstock, and particularly relates to a buttstock having an automated external defibrillator assembled therein.

2. Related Art

In order to survive and have a peaceful life territory, ancient people needed weapons, such as sharpened stones, pointed trenches, or even their fists, as tools to fight nature in order to obtain food, necessities, or to overcome threats from wild animals. As a result of human evolution and technological development, people have produced numerous kinds of shotguns with which to catch the prey efficiently, thereby achieving a multipurpose of survival as well as living space for groups and economic security.

Today, the shotgun is no longer confined to the hunter; many people, especially those in the upper classes, regard hunting as a leisure activity with historical traditions. By hunting, people can draw close to nature, relax, and learn to respect the wonder and amazement of nature. However, although hunting activities can add drama and interest to life, they also pose some health hazards. These risks, in addition to common traumas, may also include unexpected sudden cardiac death, cardiac disease resulting from age, personal history of disease, climate weathers, high strength physical activities, lack of sleep, improper diet, or can even resulting from the intense pressure and elevated emotion induced by opposing the hunting of animals.

If a person can have a first-aid treatment, for example, being treated immediately with an automated external defibrillator (hereinafter, abbreviated AED), or other auxiliary rescuing equipment, when experiencing sudden cardiac attack, the endangered person may be saved. The AED is a simple medical device provided mainly for non-medical personnel to rescue patients in danger of sudden death from cardiac arrest. The AED can automatically detect the cardiac dysrhythmia phenomena (including ventricular tachycardia and ventricular fibrillation), of the patient and instruct whether it is necessary to apply electroshocks to the heart of the patient. Cardiac arrests resulting from sudden cardiac dysrhythmias can be recovered with a success rate of 90 percent if electroshocks are applied to the cardiac arrest patient within one minute. In the public access defibrillation (PAD) program promoted in some countries, AEDs are widely recommended and fixedly assembled in public places. Nevertheless, due to the need for portability, personal first aid equipment for hunting and camping activity is quite simple and unlike the aforementioned AED equipment which is really useful for rescuing dying people; additionally, camp fields and hunting fields are commonly located in the out-of-way places; desolate, lacking medical resources, with poor telecommunication support, and challenges predicting the weather and the traffics. Anyone experiencing a cardiac arrest in such a place, has little chance of survival since the time required for professional first aid is too long.

According to the American Heart Association, some 360,000 out-of-hospital cardiac arrests occur each year in the United States, largely involving middle-aged men, with only 9.5 percent surviving. Patients can survive if they are given cardiopulmonary resuscitation (CPR) immediately and their hearts are jolted back into normal rhythm with a defibrillator.

According to the American Heart Association, most sudden cardiac arrest adults are in a state of ventricular fibrillation, with their hearts ceasing to pump blood. The treatment for ventricular fibrillation is using the defibrillation and the cardioversion procedure, namely, applying electroshock to terminate the state of ventricular fibrillation and leading the heart back into normal rhythm. It is understood that the possibility of survival decreases by about 10 percent with every minute that the defibrillation and the cardioversion procedure is delayed. Additionally, if the patient cannot be treated properly in 4 to 6 minutes, even if they can survive this cardiac arrest, their brain will suffer unrecoverable damage which may result a persistent vegetative state. However, it is unlikely that medical personnel can ever reach an unconscious person within a minute. Consequently, it is impossible to apply first aid procedures instantly to patients suffering cardiac disease, due to lack of a systematic planning to redesign the implementation methods and the structure of the AED.

The purpose of the prevent invention is to place a humane medical device within a weapon, so that the guns become mobile emergency stations which readily accompany people in adventure sports, thereby increasing the possibility for an AED to rescue a patient instantly.

SUMMARY

In view of this, the disclosure provides a buttstock including a main body and a protecting member. The main body includes a shell member and an automated external defibrillator disposed in the shell member. The protecting member is movably connecting with the shell member of the main body so as to move relative to the shell member between a first position and a second position, wherein the protecting member shields the automated external defibrillator at the first position and exposes the automated external defibrillator at the second position respectively.

As above, when a person suddenly suffers ventricular fibrillation or ventricular tachycardia in a hunting field or a camping field, another person (no matter whether their friend or rescue personnel), moves the protecting member from the first position to the second position so as to expose and operate the AED immediately, for applying electroshock to the patient's heart, and follows by applying the external cardiac massage procedures or other cardiopulmonary resuscitation procedures to give the patient first aid treatment, under which circumstances, the patient's likelihood of survival increases significantly due to proper treatment being applied to the patient before arriving in the emergency room. Furthermore, when the AED is not in use, the protecting member can be moved to the first position so as to protect the AED appropriately without affecting the use of the gun.

The detailed features and advantages of the disclosure are described below in great detail through the following embodiments, the content of the detailed description is sufficient for those skilled in the art to understand the technical content of the disclosure and to implement the disclosure there accordingly. Based upon the content of the specification, the claims, and the drawings, those skilled in the art can easily understand the relevant objectives and advantages of the disclosure.

BRIEF DESCRIPTION OF THE DRAWINGS

The disclosure will become more fully understood from the detailed description given herein below for illustration only, and thus not limitative of the disclosure, wherein.

DETAILED DESCRIPTION

Figure 1:
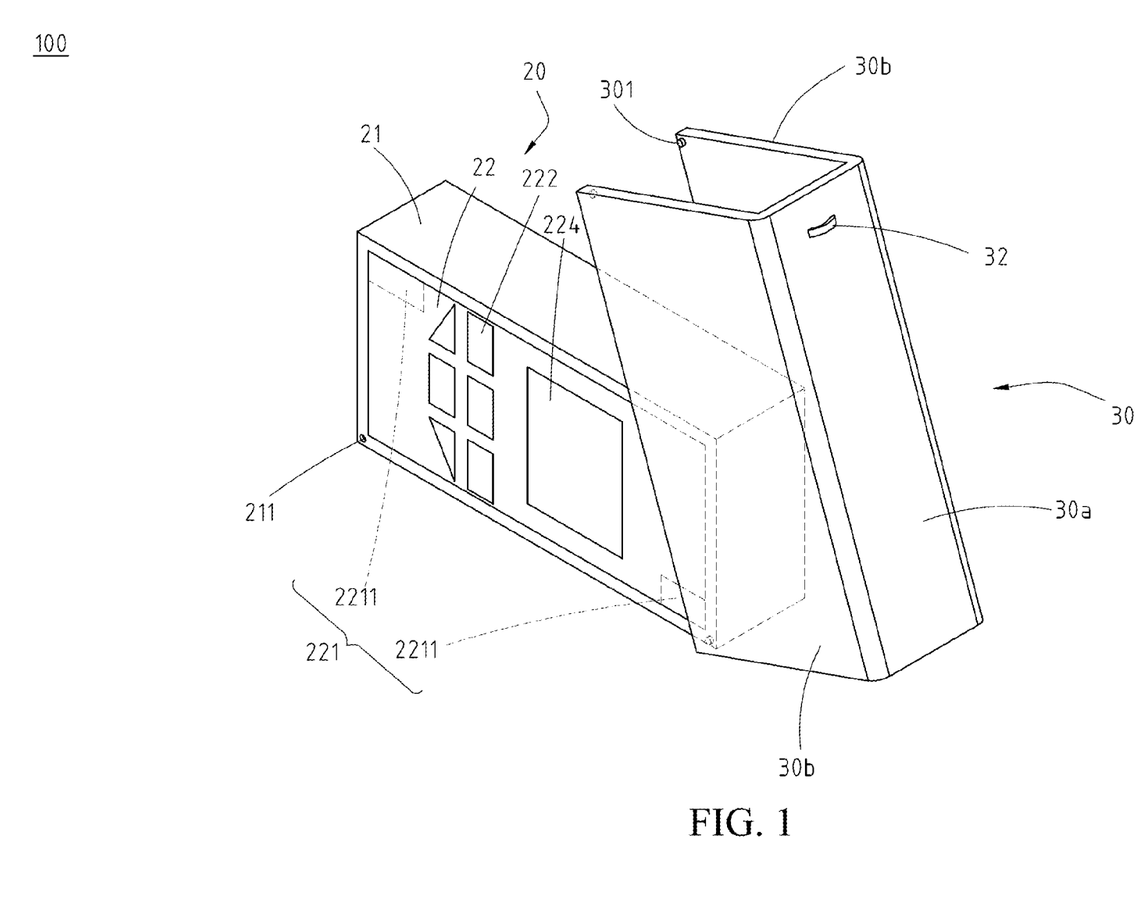
FIG. 1 is a perspective view of a buttstock of a first embodiment of the disclosure.
Figure 2A:
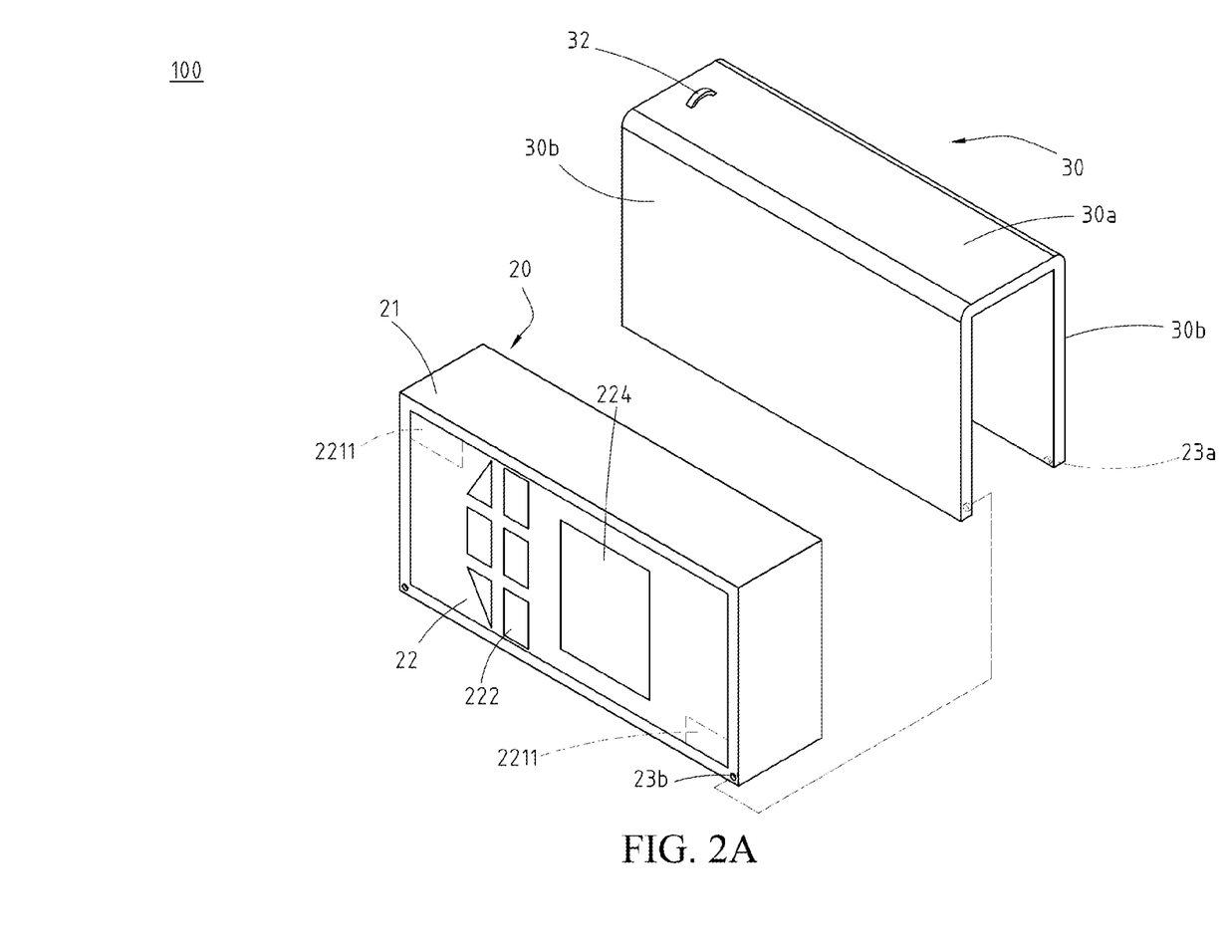
FIG. 2A is an exploded view (1) of the buttstock of the first embodiment of the disclosure.
Figure 2B:
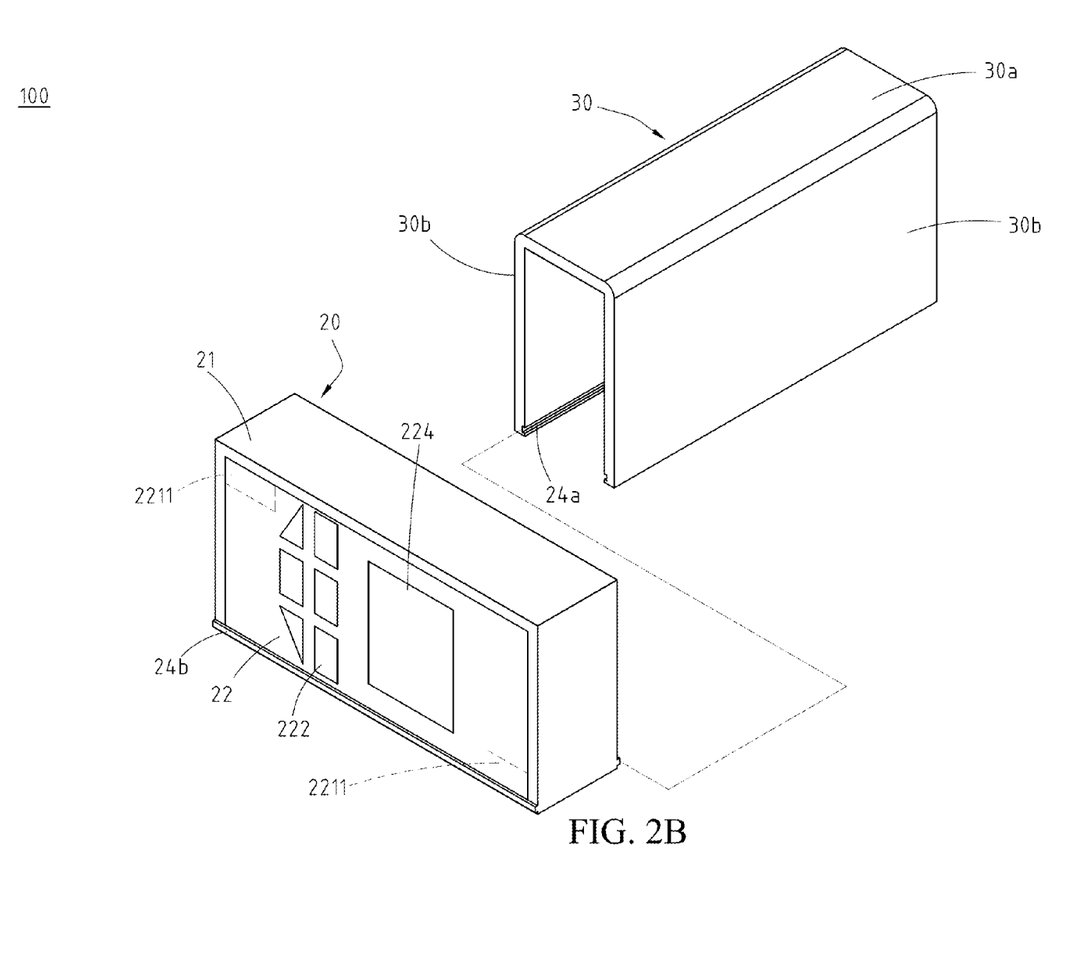
FIG. 2B is an exploded view (2) of the buttstock of the first embodiment of the disclosure.
Figure 3:
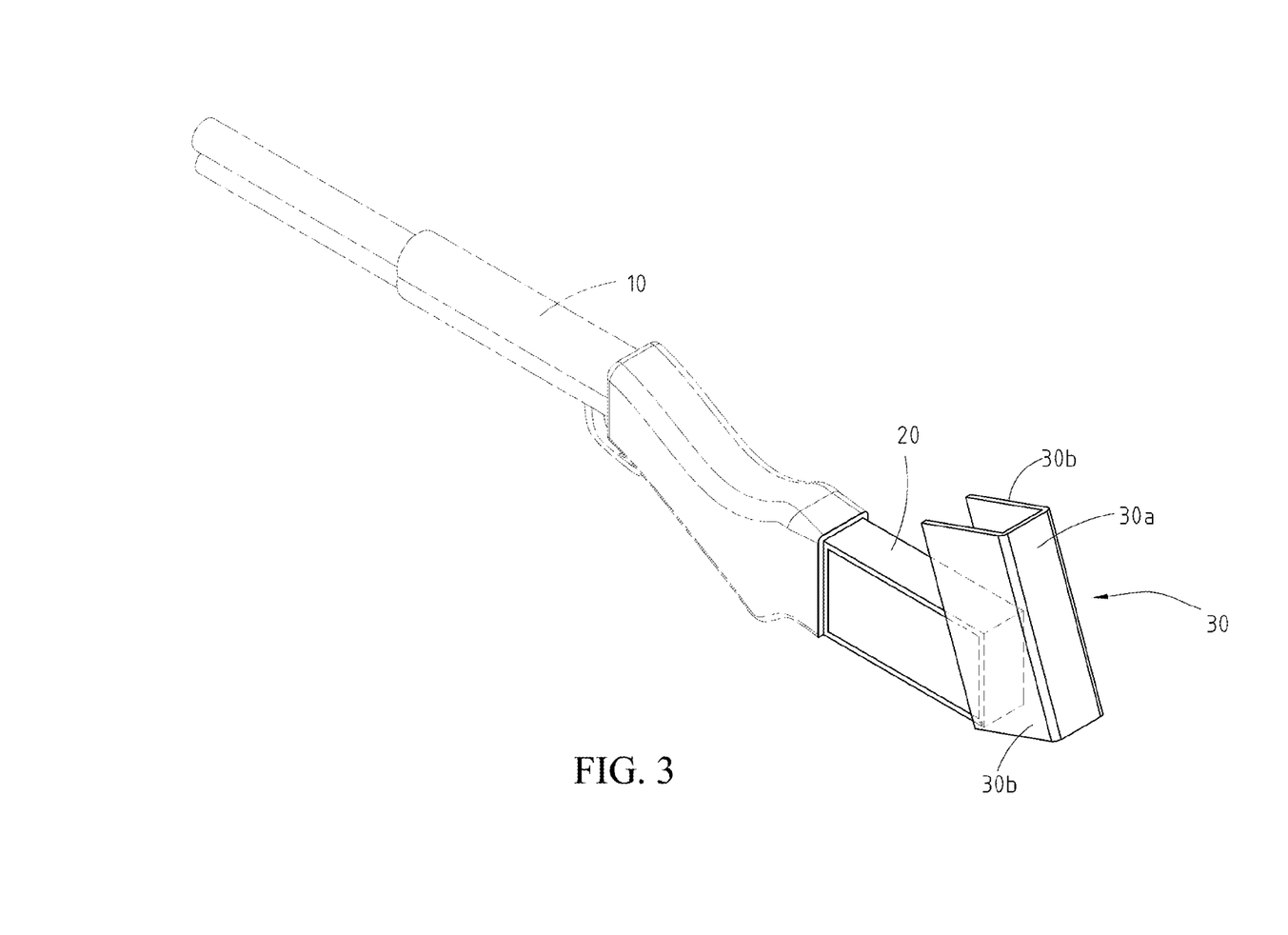
FIG. 3 is a schematic assembled view of the buttstock of the first embodiment of the disclosure.

Please refer to FIGS. 1-4B, which are respectively a perspective view, exploded views (1) and (2), a schematic assembled view, a schematic partial enlarged view and a schematic operational view of a buttstock 100 of a first embodiment of the disclosure. The buttstock 100 includes a main body 20 and a protecting member 30. The buttstock 100 can be combined with a barrel 10 to form a gun, such as a shotgun (as shown in FIG. 3), but not limited thereto; the gun can also be a toy gun, a paintball gun or other types of guns. Additionally, in this embodiment, the protecting member 30 can be moved relative to the barrel 10. The protecting member 30 has a cross section approximately formed as U-shaped; that is, the protecting member 30 has a top face 30a and two side faces 30b connected to the top face 30a in which the two side faces 30b are opposite to each other.

Please refer to FIG. 1 and FIG. 2A, in which the main body 20 includes a shell member 21 and an automated external defibrillator 22 (hereinafter, abbreviated AED 22). The AED 22 is disposed in the shell member 21 and capable of outputting an electroshock signal to an electroshock point, for example, the breast region or some particular belly regions, of a patient's heart. Accordingly, the electroshock signal from the AED 22 can stop the irregular heartbeat; meanwhile, the patient's heart is jolted back into normal rhythm with the cardiopulmonary resuscitation (CPR) procedure. In this embodiment, the AED 22 and the shell member 21 are manufactured separately with the AED 22 being received in the shell member 21, but embodiments are not limited thereto; in some implementation aspects, the shell member 21 and the AED 22 are integrally formed as a whole; in some implementation aspects, an elastic buffer member (not shown), is disposed between the shell member 21 and the AED 22 so as to absorb the impact upon shooting the gun and protect the electric components inside the AED 22 from damaging due to the impact, thereby the AED 22 can be operated normally and saving the patient's life.

Please refer to FIG. 1 and FIG. 2A again, in which the protecting member 30 is movably connecting with the shell member 21 of the main body 20 so as to move relative to the shell member 21 between a first position and a second position, wherein the protecting member 30 shields the AED 22 at the first position and exposes the AED 22 at the second position respectively. In this embodiment, the protecting member 30 is substantially the casing of the shell member 21 and can be made of metal, polymeric materials, high mechanical strength plastics or other materials with high mechanical strength. Based on this, when the AED 22 is not in use the protecting member 30 is moved to the first position so as to protect the AED 22 appropriately without affecting the using of the gun (here, when the protecting member 30 is located at the first position, the two side faces 30b of the protecting member 30 are approximately attached to the shell member 21 and shield the AED 22); when the AED 22 is required, the protecting member 30 is moved from the first position to the second position so as to expose the AED 22 for operating the AED 22 conveniently (here, when the protecting member 30 is located at the second position, the top face 30a of the protecting member 30 is disposed at a position far from the shell member 21, and most parts of the two side faces 30b are not attached to the shell member 21). Additionally, in this embodiment, when a user operates the gun, a bottom plate 30c of the protecting member 30 (that is, the portion of the protecting member 30 far from the barrel 10), is directly abutted against the user's body. In order to retard the impact from the recoil of the gun, elastic buffering members (not shown), corresponding to the stature of the user's body can also be assembled on the bottom plate 30c, so that a compactness between the user's body and the gun is improved; similarly, one side face 30b of the protecting member 30 which is contacted with the cheek of the user can also have an ergonomic cheek fitting plate (not shown), assembled thereon, thereby increasing the comfortableness of the user upon operating the gun.

Please refer to FIG. 1 and FIG. 2A, in which embodiment, via a plurality of pivoting portions 23a protruded from the protecting member 30 and a plurality of pivoting holes 23b opened on the shell member 21, the shell member 21 and the protecting member 30 are connected with each other in a pivoting manner, so that the protecting member 30 is swingable relative to the shell member 21 so as to move between the first position and the second position. Here, the pivoting portions 23a are protruded on one side of the protecting member 30 far from the barrel 10 (as shown in FIG. 3), and the pivoting holes 23b correspond to the pivoting portions 23a and are opened on one side of the shell member 21 far from the barrel 10. Based on this, one side of the protecting member 30 is pivoting with one side of the shell member 21, so that the protecting member 30 is movable relative to the shell member 21 so as to move between the first position and the second position, but embodiments are not limited thereto; in some implementation aspects, the pivoting portions 23a are protruded from other portions of the protecting member 30, and the pivoting holes 23b are correspondingly opened on other portions of the shell member 21; alternatively, in some implementation aspects, the pivoting portions 23a are disposed on the shell member 21 and the pivoting holes 23b are opened on the protecting member 30. Additionally, in some implementation aspects, the protecting member 30 and the shell member 21 of the main body 20 are movably connected with each other via slide grooves 24a and slide rails 24b (as shown in FIG. 2B).

Please refer to FIG. 1 and FIG. 2A, in which in some implementation aspects, the shell member 21 further includes a positioning portion 211 and the protecting member 30 further includes a limiting portion 301. The positioning portion 211 is selectively combined with or detached from the limiting portion 301 so as to release the protecting member 30 for moving from the first position to the second position. In this embodiment, the positioning portion 211 and the limiting portion 301 are engaging structures corresponding to each other, but embodiments are not limited thereto; the positioning portion 211 and the limiting portion 301 can be corresponding locking structures, buckling structures, magnetic attaching structures, and so forth. Here, the positioning portion 211 and at least one of the pivoting holes 23b are respectively disposed at two opposite ends of the same side of the shell member 21; similarly, the limiting portion 301 and at least one of the pivoting portions 23a are respectively disposed at two opposite ends of the same side of the protecting member 30, so that when the protecting member 30 is located at the first position, the positioning portion 211 and the limiting portion 301 are combined with each other. Accordingly, when the AED 22 is not in use, the protecting member 30 is ensured to be securely positioned at the first position so as to shield and protect the AED 22. Furthermore, in order to move the protecting member 30 between the first position and the second position conveniently, the protecting member 30 further includes a poking block 32 provided for moving the protecting member 30 conveniently. Here, the poking block 32 is disposed at one face of the protecting member 30 corresponding to the moving direction of the protecting member 30 (that is, disposed at the outer surface of the top face 30a).

Please refer to FIG. 1, FIG. 2A, FIG. 4A and FIG. 4B, in which the AED 22 includes an electroshock module 221 and a control module 222. In this embodiment, the electroshock module 221 includes a plurality of conductive plates 2211 disposed at the outer surface of the AED 22 and electrically connected to the control module 222 via wires (not shown). Based on this, the buttstock 100 is attached on the electroshock point of the patient's heart upon operation, so that the conductive plates 2211 are attached on the electroshock point of the patient's heart and an electroshock loop is formed between the patient's heart and the AED 22, thereby the electroshock signal is delivered to the patient's heart. In this embodiment, the conductive plates 2211 and the control module 222 are located at different outer surfaces of the AED 22, and the conductive plates 2211 are arranged diagonally, but embodiments are not limited thereto.

In some implementation aspects, the AED 22 further includes a physiological information collecting module 2213 provided for collecting a physiological information (such as, pulse, heartbeat, blood pressure, etc.), from a person's body (the person might be the patient, but not limited thereto). For instance, the physiological information collecting module 2213 can be disposed in the electroshock module 221 so as to obtain the pulse or the heartbeat of the patient; or, the physiological information collecting module 2213 can also be disposed out of the electroshock module 221 (as shown in FIG. 4A), for measuring physiological information including aforementioned physiological information (namely, pulse and heartbeat), and other physiological information, such as temperature, oxygen concentration in the blood, and so forth.

The control module 222 is electrically connected to the electroshock module 221 so as to control the output of the electroshock signal or the input of the physiological information. Here, the control module 222 includes a processor (not shown), and an operating module (not shown), provided for controlling the processor. For example, in this embodiment, the operating module is a plurality of solid buttons provided for manually or automatically controlling the intensity, the frequency, the electroshock mode, the applied times or other parameters of the electroshock signal, or for controlling the types of the physiological information to be collected from the patient, but embodiments are not limited thereto. In some implementation aspects, the operating module can be a plurality of or a single virtual buttons, solid toggles, knobs or can be a remote controller. Here, the conductive plates 2211 are made of electrically conductive materials, such as stainless steels or conductive polymers, but embodiments are not limited thereto.

Figure 4A:
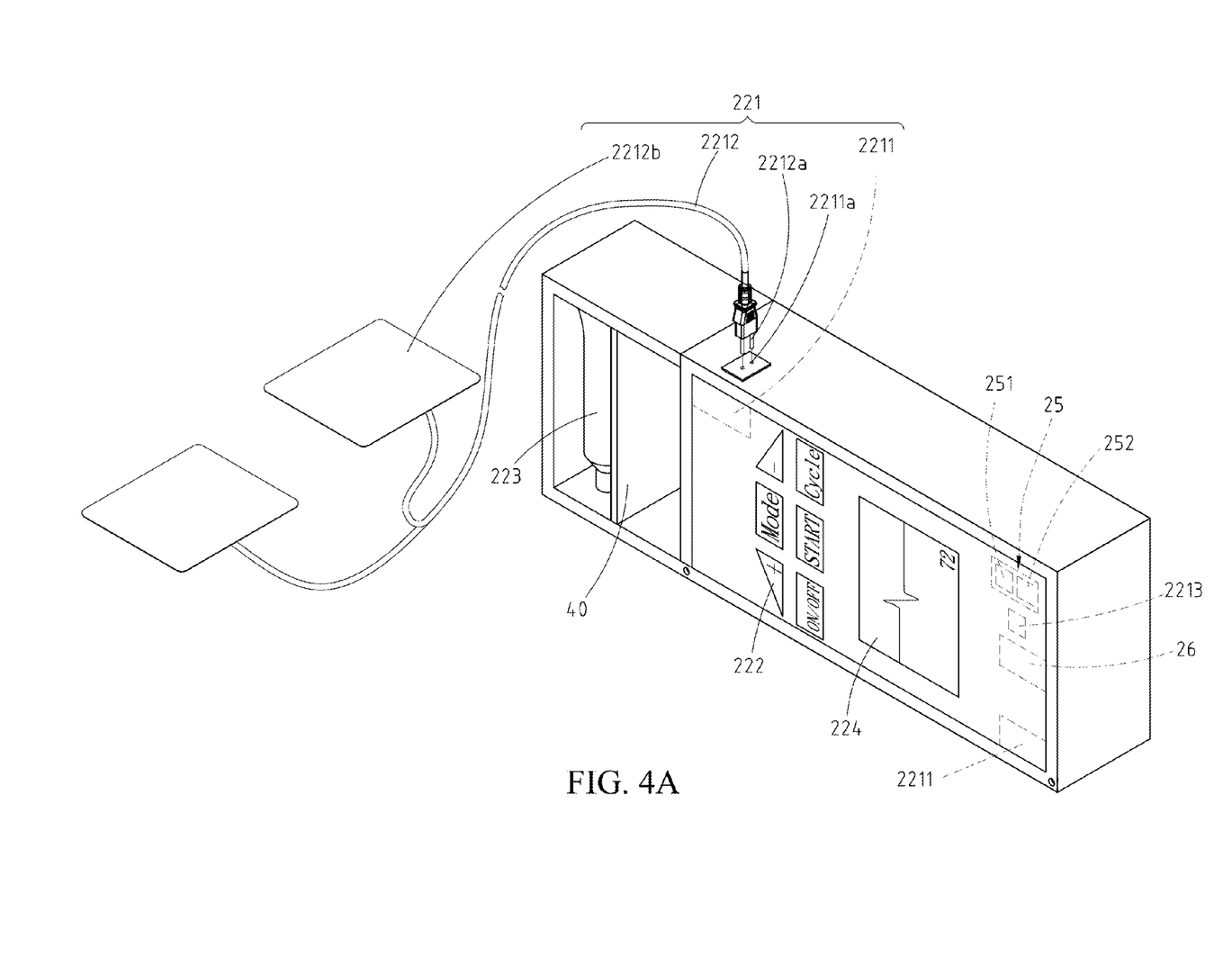
FIG. 4A is a schematic partial enlarged view of the buttstock of the first embodiment of the disclosure.
Figure 4B:
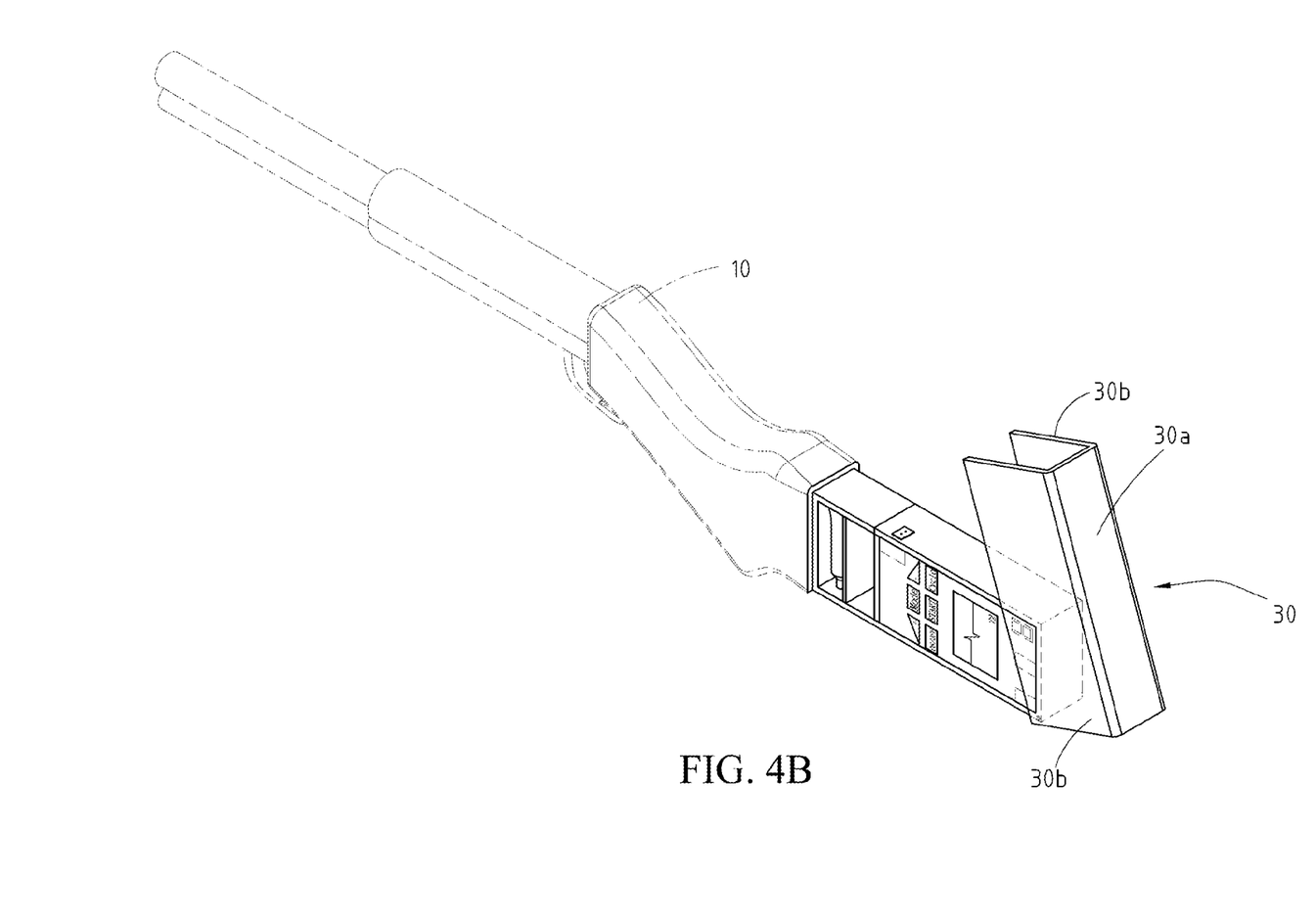
FIG. 4B is an schematic operational view of the buttstock of the first embodiment of the disclosure.

Please refer to FIG. 4A and FIG. 4B, in which the AED 22 further includes an auxiliary electroshock member 2212. The auxiliary electroshock member 2212 has a connecting end 2212a and a working end 2212b. The connecting end 2212a is detachably electrically connected to the AED 22, and the working end 2212b has an electroshock attaching plate assembled thereon and provided for attaching with the electroshock point of the patient' heart. It is understood that, although the AED 22 shown in FIG. 4A has one connecting end 2212a and two working ends 2212b, but embodiments are not limited thereto; in some implementation aspects, the AED 22 includes two or more auxiliary electroshock member 2212, and each of the auxiliary electroshock members has one connecting end 2212a and one working end 2212b. Here, for example, the AED 22 has an inserting hole 2211a or other fixing structures so as to detachably fix the connecting end 2212a of the auxiliary electroshock member 2212. As shown in FIG. 4A and FIG. 4B, the AED 22 has the inserting hole 2211a so as to fastened with the connecting end 2212a, but embodiments are not limited thereto. In this embodiment, the auxiliary electroshock member 2212 is substantially a flexible cable member and can be received in the buttstock 100 along with the AED 22. Furthermore, as shown in FIG. 4A and FIG. 4B, the connecting end 2212a can be an inserting structure with a plurality of plugs (here, the connecting end 2212a is an inserting structure with two banana jacks) and fool-proof designed, but embodiments are not limited thereto. For example, the connecting end 2212a may have another appearance capable of fastened with the AED 22 securely. When the connecting end 2212a of the auxiliary electroshock member 2212 is inserted into the AED 22, the conductive plates 2211 are disconnected to the electroshock module 221, so that the electroshock signal is provided from the working ends 2212b of the auxiliary electroshock member 2212. Hence, an alternative connecting means is provided with respect to attaching the conductive plates 2211 on the electroshock point of the patient's heart, thereby delivering the electroshock signal to the electroshock point of the patient's heart through the auxiliary electroshock member 2212. In other words, in the disclosure, the conductive plates 2211 and the auxiliary electroshock member 2212 are alternatives to each other and can be selectively applied according to the operation of the user.

In some implementation aspects, the AED 22 further includes a conductive adhesive 223; for example, the conductive adhesive 223 is received in a flexible container or a can, but embodiments are not limited thereto. Based on this, via the application of the conductive adhesive 223, the conductivity of the electroshock point of the skin of the patient is increased so that the electroshock signal is concretely applied to the electroshock point of the patient's heart (for instance, the conductive adhesive 223 is applied to the patient whose skin is too dry to conduct so as to increase the conductivity of the patient's skin and provides a function of skin protecting and temperature reducing to the patient's skin). In this embodiment, the buttstock 100 further includes at least a space-separating member 40 formed platy and disposed in the shell member 21 so as to define a plurality of receiving spaces for receiving the AED 22 and the auxiliary electroshock member 2212. In this embodiment, the number of the space-separating members 40 is two, and the two space-separating members 40 are approximately disposed parallel to define three receiving spaces. As shown in FIG. 4A and FIG. 4B, in this embodiment, the auxiliary electroshock member 2212, the conductive adhesive 223 and the AED 22 are respectively disposed in the three receiving spaces, but embodiments are not limited thereto. The number, the alignment and the shape of the space-separating members 40, and the respective spatial relationship between the aforementioned components (namely, the auxiliary electroshock member 2212, the conductive adhesive 223, the AED 22, etc.), can be adjusted and varied; for example, in some implementation aspects, the number of the space-separating member 40 is reduced to one, with the auxiliary electroshock member 2212 and the conductive adhesive 223 being received in one receiving space, and the AED 22 being received in another receiving space.

Please refer to FIG. 4A and FIG. 4B again, in which the AED 22 further includes a display module 224 electrically connected to the control module 222 and the electroshock module 221. The display module 224 selectively displays at least a physiological parameter of the patient, at least an output parameter of the electroshock signal or the combination thereof (for example, the display module 224 displays the pulse, the heartbeat, the temperature, the electrocardiogram or other physiological parameters of the patient; in this embodiment, the display module 224 displays the heartbeat and the electrocardiogram of the patient, as shown in FIG. 4A). In this embodiment, the display module 224 is a LCD disposed in the shell member 21 so as to display the aforementioned parameters numerically or graphically, so that the instant physiological condition of the patient can be understood, but embodiments are not limited thereto; the display module 224 can be other types of display screens or LED emitting elements. Furthermore, here, the number of the display module 224 is one, but embodiments are not limited thereto.

Please refer to FIG. 4A and FIG. 4B again, in which the main body 20 further includes a power device 25 disposed in the shell member 21 and electrically connected to the AED 22. It is understood that the power device 25 is optionally disposed out of the AED 22 or in the AED 22, embodiments are not limited thereto. Here, the power device 25 can be a disposable battery or a rechargeable battery; for example, the power device 25 can be, but not limited to, a zinc-carbon battery, an alkaline battery, a nickel-metal hydride battery, a lithium battery, and so forth. The power device 25 includes a power output portion 251 assembled on the shell member 21 and electrically connectable with an outer electric device (such as a cell phone or a gun having the buttstock 100 of the disclosure). Based on this, the power device 25 outputs electricity to the outer electric device for operation. Please refer to FIG. 4A and FIG. 4B, the power device 25 includes a power input portion 252 assembled on the shell member 21 and electrically connectable to an outer power source so as to receive electricity from the outer power source for charging the power device 25. The outer power source can be the supply mains or a portable power supplying device. Accordingly, the power device 25 in the main body 20 is charged by the outer power source via the power input portion 252.

Additionally, please refer to FIG. 4A and FIG. 4B again, the main body 20 further includes a signal emitting system 26 electrically connected to the AED 22. In some implementation aspects, the signal emitting system 26 automatically emits a signal to rescue personnel upon the AED 22 is operating, so that the rescue personnel will arrive to the place where the signal is emitted from as soon as possible, but embodiments are not limited thereto. For example, the signal emitting system 26 can be provided to related departments for tracing or locating the guns so as to manage the guns. In some implementation aspects, the signal emitting system 26 is not linked to the AED 22 but linked to a switch (not shown), disposed on the buttstock 100, so that the user directly operates the switch to launch the signal emitting system 26 for emitting the signal and does not launch the signal emitting system 26 by mistake upon operating the AED 22. It is understood that the signal emitting system 26 can have an antenna or apply the barrel 10 of the gun as the antenna for emitting the signal. Here, the signal is a wireless electric wave signal, but is not limited thereto.

Figure 5:
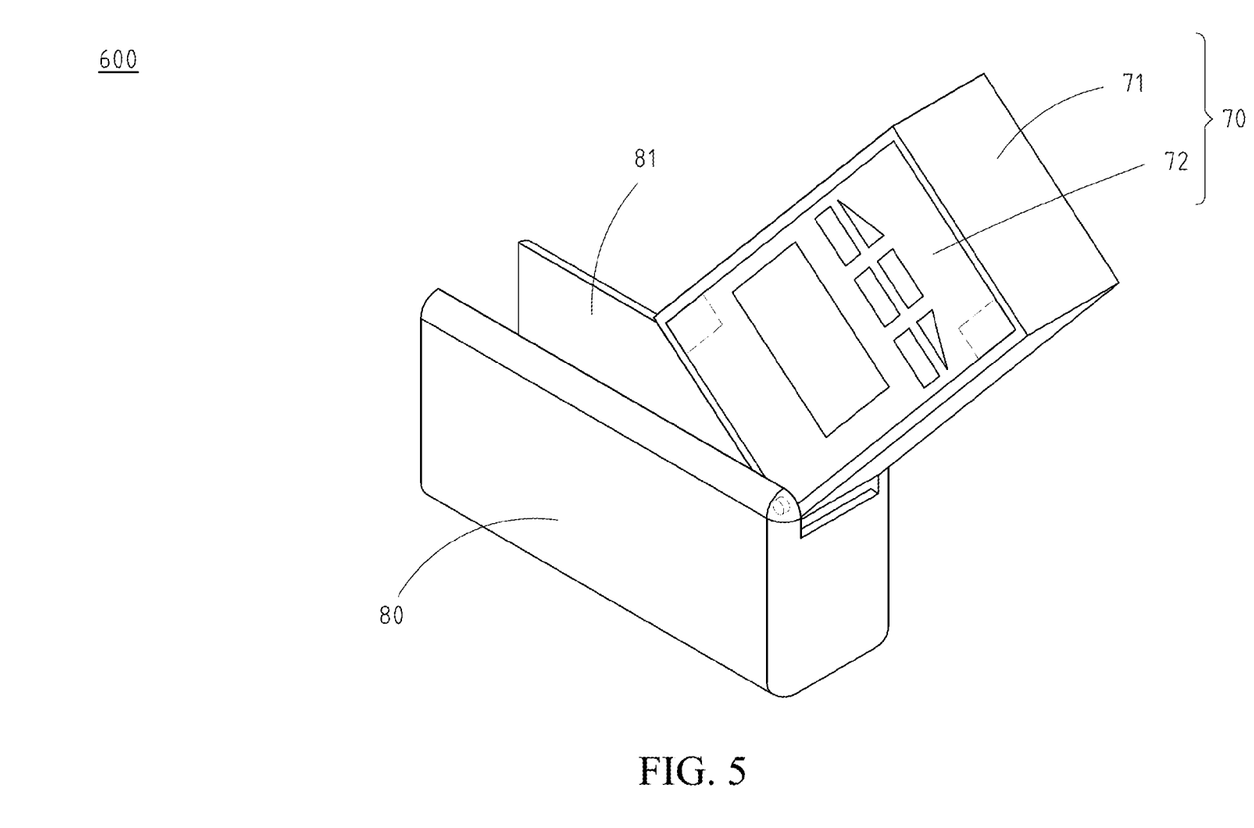
FIG. 5 is a perspective view of a buttstock of a second embodiment of the disclosure.
Figure 6:
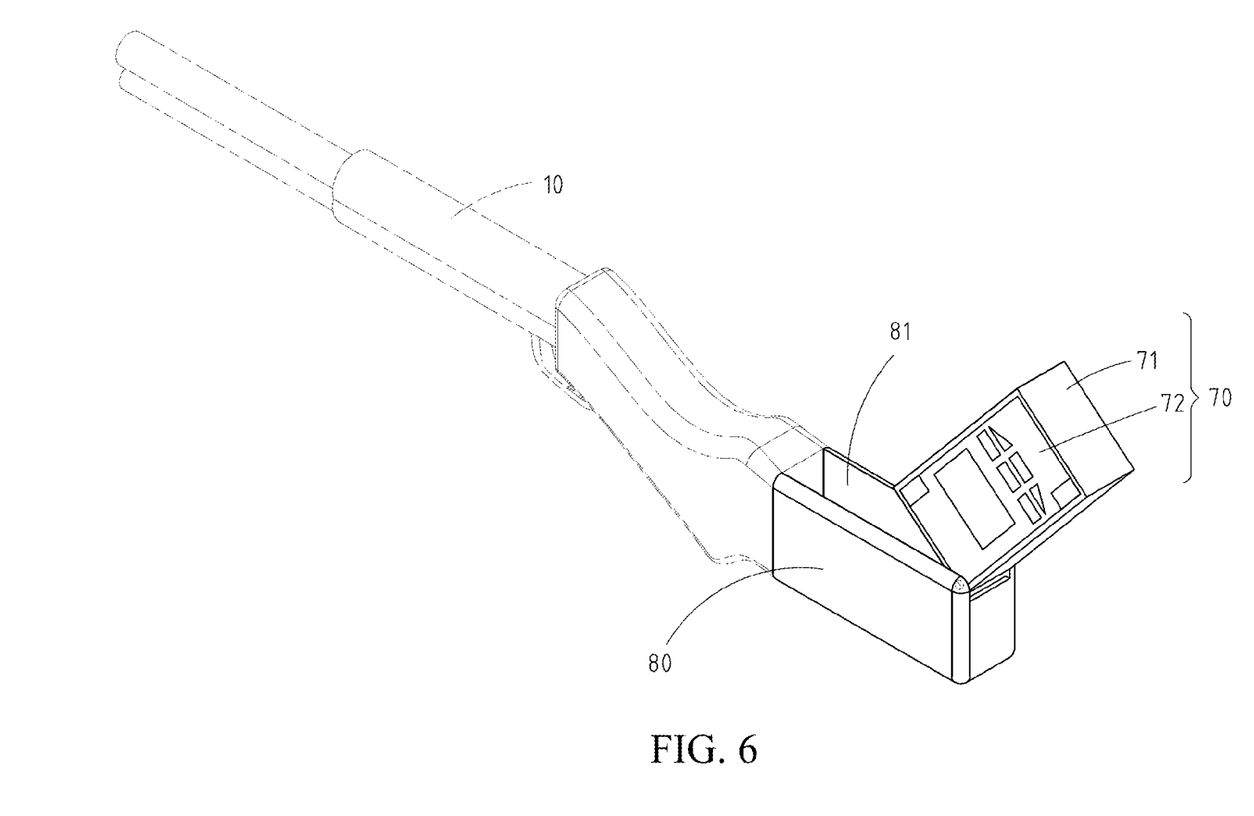
FIG. 6 is a schematic assembled view of the buttstock of the second embodiment of the disclosure.

Please refer to FIG. 5 and FIG. 6, which are respectively a perspective view and a schematic assembled view of a buttstock 600 of a second embodiment of the disclosure. The structure of the buttstock 600 of the second embodiment is approximately similar to that of the first embodiment, except that in the first embodiment, the protecting member 30 is movable relative to the barrel 10; in this embodiment, the main body 70 is movable relative to the barrel 10. Please refer to FIG. 5 and FIG. 6, in which embodiment the protecting member 80 has a receiving groove 81 opened thereon so as to receive the shell member 71 with the AED 72 being received in the shell member 71. Hence, the protecting member 80 is movable relative to the shell member 71 between the first position and the second position, wherein the protecting member 80 shields the AED 72 at the first position and exposes the AED 72 at the second position.

Figure 7:
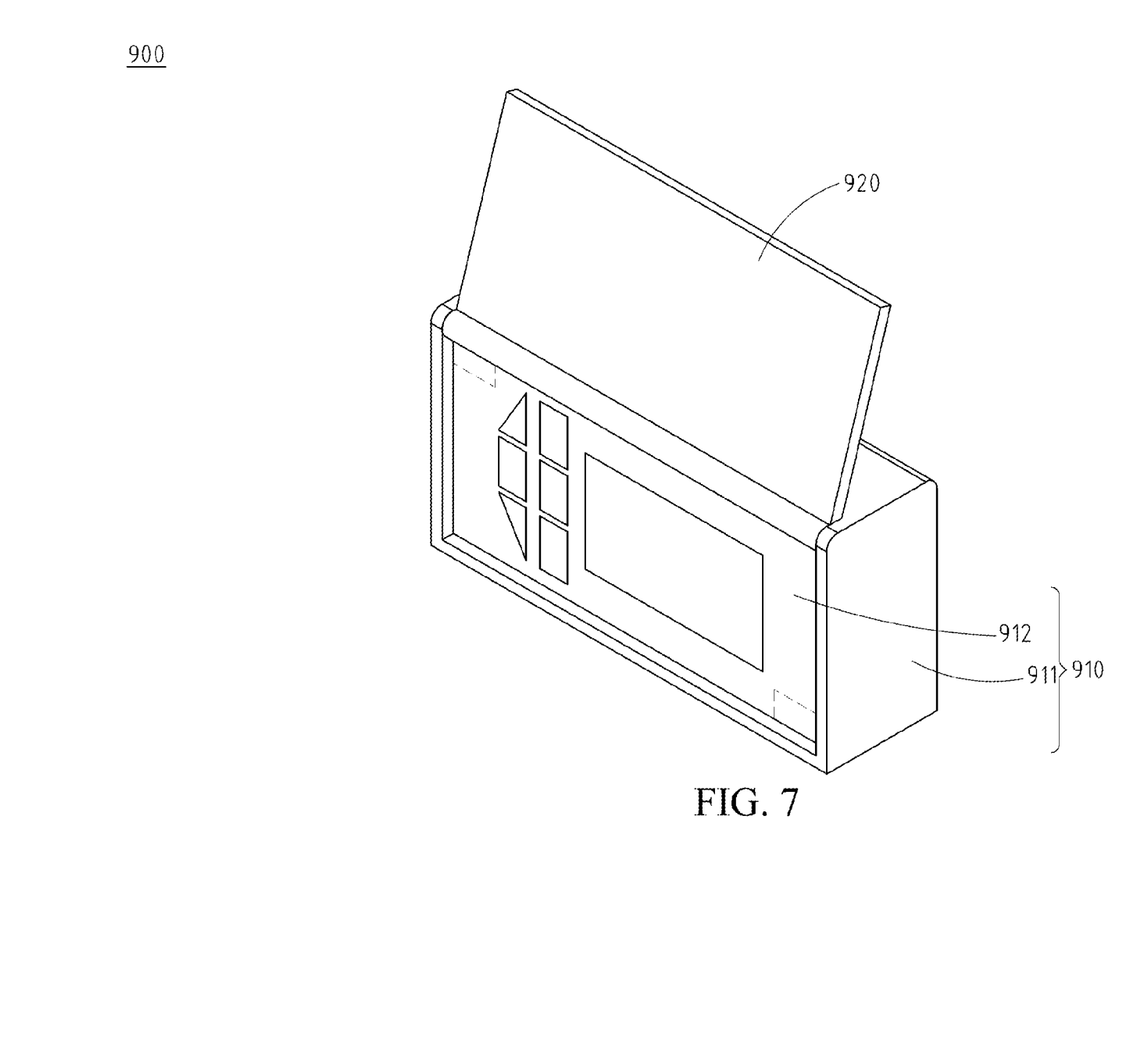
FIG. 7 is a perspective view (1) of a buttstock of a third embodiment of the disclosure.
Figure 8:
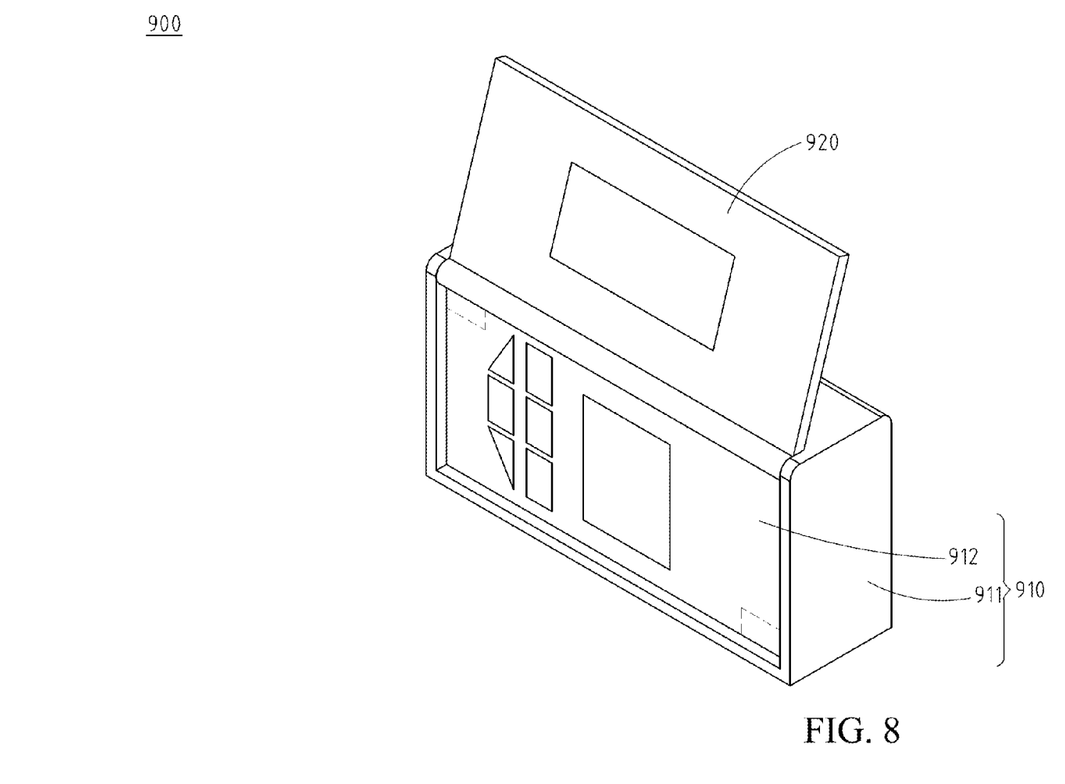
FIG. 8 is a perspective view (2) of the buttstock of the third embodiment of the disclosure.
Figure 9:
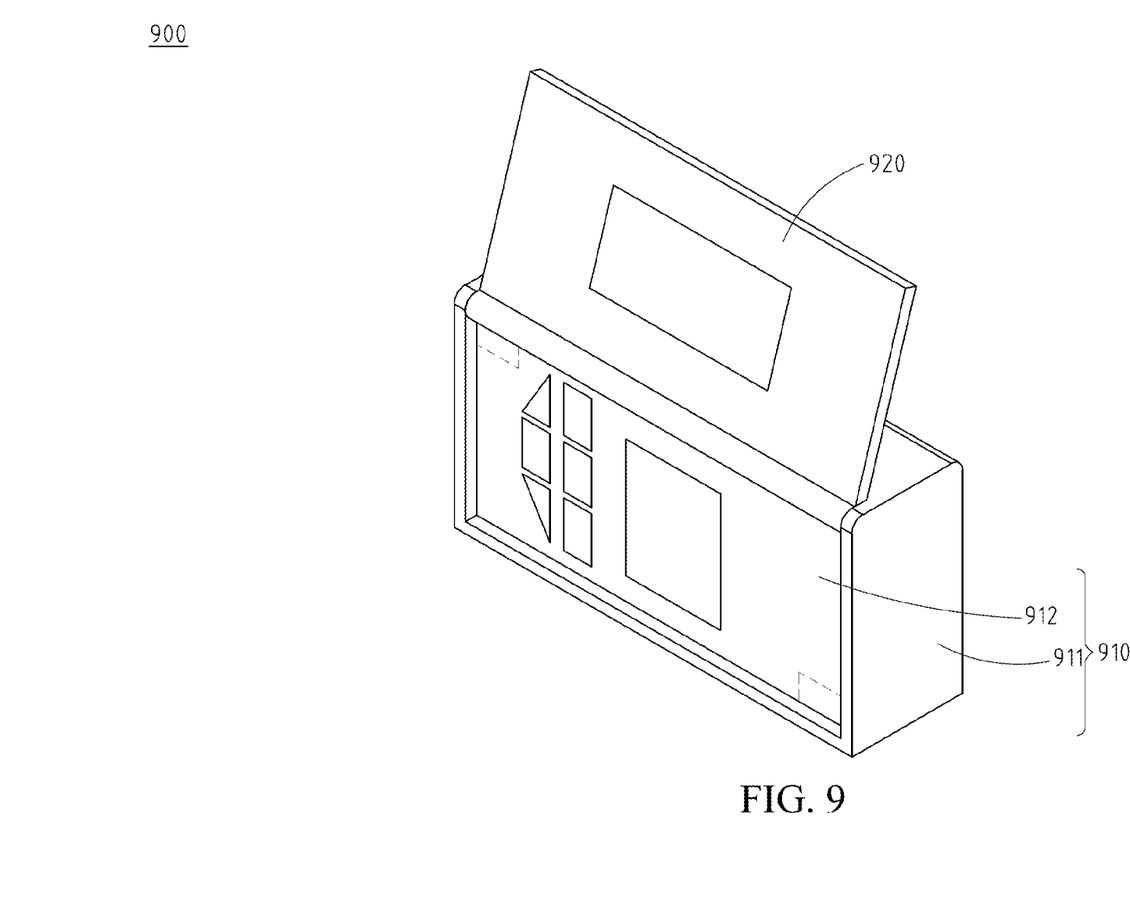
FIG. 9 is a perspective view (3) of the buttstock of the third embodiment of the disclosure.

Please refer to FIG. 7, FIG. 8 and FIG. 9, which are respectively perspective views (1), (2) and (3) of a buttstock 900 of a third embodiment of the disclosure. The structure of the buttstock 900 of the third embodiment is approximately similar to that of the first embodiment, except that in this embodiment, the protecting member 920 does not have the U-shape cross section but is a plate; here, the protecting member 920 is disposed at only one end of the shell member 911 of the main body 910 rather than shielding the two sides of the shell member 21 as disclosed in the first embodiment. Here, the protecting member 920 is movably connected with the shell member 911 of the main body 910 via a pivoting manner so as to move relative to the shell member 911 between a first position and a second position, so that the protecting member 920 shields the AED 912 at the first position and exposes the AED 912 at the second position respectively. That is, the protecting member 920 is a covering member with one side thereof pivotally connected with the corresponding one side of the shell member 911, but embodiments are not limited thereto; in some implementation aspects, the protecting member 920 and the shell member 911 respectively includes slide rails and slide grooves (not shown), so that the protecting member 920 is movable between the first position and the second position via the slide rails and the slide grooves. Additionally, besides built in the AED 22 as described above, the display module 224 can be externally connected to the AED 22; that is, as shown in FIGS. 7-9, besides being disposed on the shell member 911, the display module 224 can be disposed on the protecting member 920 or be disposed on not only the shell member 911 but also the protecting member 920.

As above, when somebody suddenly suffers ventricular fibrillation or the ventricular tachycardia in a hunting field or camping field, another person (whether their friend or rescue personnel), moves the protecting member from the first position to the second position so as to expose and operate the AED immediately, to apply electroshock to the patient's heart, and followed by applying external cardiac massage procedures or other cardiopulmonary resuscitation procedures to give the patient first aid treatment, under which circumstances the patient's likelihood of survival are increased significantly due to proper treatment being applied to the patient before arriving in the emergency room. Additionally, when the AED is not in use, the protecting member can be moved to the first position so as to protect the AED appropriately without affecting the using of the gun.

While the disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A buttstock, comprising:
   a main body, comprising:
   a shell member; and
   an automated external defibrillator disposed in the shell member, wherein the automated external defibrillator comprises:
   an electroshock module comprising a plurality of conductive plates arranged separately at the outer surface of the automated external defibrillator, the electroshock module being capable of outputting an electroshock signal through the conductive plates; and
   a control module electrically connected to the electroshock module so as to control the output of the electroshock signal;
   a display module electrically connected to the control module and the electroshock module, wherein the display module selectively displays at least a physiological parameter of a patient, at least an output parameter of the electroshock signal, or the combination thereof;
   an auxiliary electroshock member having a connecting end and a working end, wherein the connecting end is detachably electrically connected to the automated external defibrillator, the working end has an electroshock attaching plate assembled thereon and provided for attaching with an electroshock point of the heart of the patient; and
   a power device disposed in the shell member and electrically connected to the automated external defibrillator, wherein the power device comprises:
   a power output portion assembled on the shell member and electrically connectable to an outer electric device so as to provide electricity to the outer electric device
   a power input portion assembled on the shell member and electrically connectable to an outer power source so as to receive electricity from the outer power source for charging the power device; and
   a protecting member, movably connecting with the shell member of the main body so as to move relative to the shell member between a first position and a second position, wherein the protecting member shields the automated external defibrillator at the first position and exposes the automated external defibrillator at the second position respectively.

2. The buttstock according to claim 1, wherein the shell member further comprises a positioning portion, the protecting member further comprises a limiting portion, and the positioning portion is selectively combined with or detached from the limiting portion so as to release the protecting member for moving from the first position to the second position.

3. The buttstock according to claim 1, wherein one side of the shell member has a plurality of pivoting holes opened thereon, one side of the protecting member has a plurality of pivoting portions disposed thereon, and the pivoting portions correspond to the pivoting holes.

4. The buttstock according to claim 1, wherein the protecting member is platy, disposed at one end of the shell member, and movably connected to the shell member, wherein the automated external defibrillator is exposed from one end of the shell member.

5. The buttstock according to claim 1, wherein the main body further comprises a signal emitting system electrically connected to the automated external defibrillator, so that the signal emitting system automatically emits a signal upon the automated external defibrillator is operating, and the signal emitting system applies a barrel connected to the buttstock as an antenna for emitting the signal.

6. The buttstock according to claim 1, wherein the main body further comprises a signal emitting system provided for emitting a signal, and the signal emitting system applies a barrel connected to the buttstock as an antenna for emitting the signal.

* * * * *